United States Patent [19]

Marcus

[11] Patent Number: 4,813,939

[45] Date of Patent: Mar. 21, 1989

[54] WINGED INFUSION APPARATUS FOR PATIENT IMPLANTABLE ACCESS PORTS

[76] Inventor: Joel Marcus, 41 Ascot Dr., Wayside, N.J. 07712

[21] Appl. No.: 128,869

[22] Filed: Dec. 4, 1987

[51] Int. Cl.$^4$ ............................................. A61M 5/32
[52] U.S. Cl. .................................. 604/177; 604/174; 604/175
[58] Field of Search ...................... 604/174, 175, 177

[56] References Cited

U.S. PATENT DOCUMENTS

| | | | |
|---|---|---|---|
| 3,856,020 | 12/1974 | Kovac | 604/177 |
| 4,235,234 | 11/1980 | Whitney et al. | 604/177 |
| 4,645,495 | 2/1987 | Vaillancourt | 604/177 |
| 4,710,176 | 12/1987 | Quick | 604/177 |
| 4,743,231 | 5/1988 | Kay et al. | 604/177 |

Primary Examiner—C. Fred Rosenbaum
Assistant Examiner—Gene B. Kartchner
Attorney, Agent, or Firm—Arthur L. Plevy

[57] ABSTRACT

There is disclosed a winged infusion apparatus for use with patient implantable access ports. Essentially, the apparatus includes a composite disc housing which is circular in configuration and has integrally formed therewith two winged sections which overlie arcuate apertures in the sides of the disc. A cannula is embedded within the internal body of the disc, and via a right angle bend the cannula emanates from the bottom surface of the disc at a central location. The winged members are operable so that they can be grasped by a user and placed in an upright position via integral hinges associated with each winged member. In this manner the user can then insert the cannula into an axis port which is implanted in a suitable body cavity of a patient and which has an output aperture on the patient's skin. By utilizing the device and due to the fact that the needle is centrally located and based on the position of the winged members, the entire unit has an extremely uniform profile whereby once the winged members are utilized in an upright position as manipulated by the fingers of a practitioner, they spring back so that they are flush with the top surface of the disc. Once the cannula is emplaced into the access port of the patient, the entire unit is taped by means of a suitable surgical tape onto the skin of the patient to thereby hold the entire unit in a rigid and fixed position.

16 Claims, 2 Drawing Sheets

WINGED INFUSION APPARATUS FOR PATIENT IMPLANTABLE ACCESS PORTS

BACKGROUND OF THE INVENTION

This invention relates generally to infusion sets and more particularly to a winged infusion set which is employed to operate in conjunction with patient implantable access ports.

The prior art is replete with a number of devices which essentially includes a cannula or needle. The cannula projects from a cylindrical member and is normally coupled to a tube. The cannula is inserted into an orifice which is associated with a port of an access device which device is directly implanted into the chest or body cavity of a patient. In this manner, the access port protrudes or is positioned on the chest or other area of the patient and has an aperture into which the cannula of the infusion device is inserted. The infusion device via the cannula is coupled to a tubing or other suitable apparatus to enable one to administer drugs or chemotherapy directly into the vascular system of the patient.

In any event, as indicated, the prior art is replete with a number of such devices. The devices of the prior art essentially consist of an elongated tube. The end of the tube has the cannula protruding therefrom. The tube is associated with two flaps or gripping means which are coupled to and protrude from the body of the tube. Essentially, the gripping means enables a practitioner such as a nurse or physician to insert the cannula into the access port associated with the patient. In any event, as one can ascertain, the prior art devices include gripping means which are fairly substantial and which protrude substantially from the surfaces of the device.

When such a device is employed and after cannula insertion, the device and gripping means are usually taped to the body of the patient to hold the cannula and the tubing apparatus in place prior to the administration of such chemicals or other materials.

It is immediately apparent when reviewing the prior art subject matter that the cannula as protruding from the tubular member is positioned in such a manner that it can move or rotate quite freely. Due to this movement, there can be a consequent damaging of the implantable port associated with the patient thus resulting in infection or requiring another operation to remove or replace the same. In a similar manner, the gripping means consists of left and right extensions emanating from the device and when taped to the body of the patient can cause irritation as well as infection due to the fact that these gripping means are utilized by third parties to administer the chemical treatment.

In this manner, various infections can occur and so on. Thus the prior art devices can cause contamination of the surface of the patient's skin as well as providing a relatively high profile and therefore being subject to inadvertent misalignment or inadvertent dislodging. The prior art devices also can be accidentally or inadvertently dislodged because of the location of the needle or cannula with respect to the main body of the infusion device.

Furthermore, the profile of the prior art devices is such that once the prior art device is emplaced, there is required a great deal of taping in order to firmly secure the entire apparatus to the skin of the patient.

It is therefore an object of the present invention to provide an infusion set to be utilized with an implantable access port which infusion set has gripping means which essentially provide a flat profile and which do not in any manner operate to contact the skin of the patient as the cannula associated with the device is emplaced.

It is a further object of this invention to provide an infusion device having a symmetrical central body through which a cannula needle extends from the center of the body. In this manner, providing a centered position prevents rocking of the needle as placing the center of gravity over the top of the access port.

It is a further object of this invention to provide an infusion set which has easy gripping wings to enable easy insertion and removal of the apparatus once emplaced in an implantable port.

It is still a further object of this invention to provide an improved and simple infusion apparatus for utilization with patient implantable access ports.

BRIEF DESCRIPTION OF THE PREFERRED EMBODIMENT

An infusion apparatus for use with an implantable access port which port is positioned on a body surface of a patient to allow the patient to receive various fluids and chemicals for treatment, comprising a disc housing assembly having a top and bottom surface separated by a circumferential sidewall, a cannula imbedded in said disc for a given length and extending from the central region of said bottom surface and adapted to be inserted into said access port, first and second winged members hingedly secured to said top surface of said disc and oriented so that in a first position they are relatively flush with said surface and contained within said surface area and capable of being grasped so that in a second position they are positioned transverse to said surface to allow insertion of said needle of said cannula into said access port, wherein when said winged members are released they spring back to assume said first position.

DETAILED DESCRIPTION OF THE FIGURES

Figure 1:
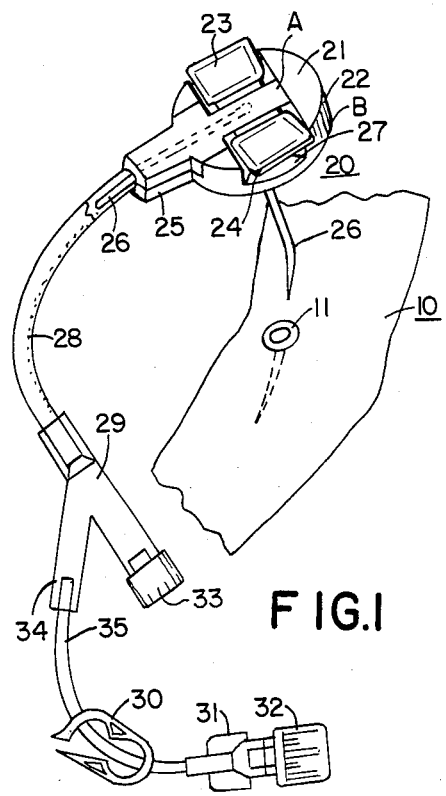
FIG. 1 is a perspective plan view depicting a winged infusion apparatus according to this invention.

Referring to FIG. 1, there is shown an perspective plan view of a winged infusion apparatus according to this invention.

The winged infusion apparatus 20 as will be explained essentially consists of a composite disc arrangement (A and B) and a cannula 26. The main body of the disc which is circular in configuration consists of a section B and a section A which are firmly secured together by means of a plastic welding technique, such as ultrasonic welding or by means of a suitable epoxy or glue. Essentially, as one can ascertain, the entire unit is manifested by having a flat profile which is best seen in the side view shown for example in FIG. 2.

The unit is associated with a left and a right wing member as 23 and 24. The wing members are coupled to the section A of the unit by means of integral hinges 40 and 41 which can be best seen in FIG. 3. The hinge members are implemented by means of the plastic injection molding technique by utilizing a scored line or thinner layer of material at the peripheral edges of each of the winged members as 23 and 24.

There is an aperture in the composite body which accommodates a cannula or a needle 26. The needle 26 is directed from the center of the disc shaped unit as shown for example in FIG. 1 and as can be best seen in FIG. 4. In this manner, the cannula 26 is directed from the geometric center of the disc and this therefore reduces the possibility of accidental or inadvertent dislodging of the needle 26. While the disc is shown as circular in configuration, many other configurations can be employed as square, rectangular and so on as long as the corners are rounded. See FIG. 4 dashed line C. Movement of the unit is reduced because of the location of the needle 26 as being centered directly at the center point of the disc 20. The centered position prevents rocking of the device by assuring that the center of gravity of the needle is directly over the top of the access port 11.

As shown in FIG. 1, there is a partial view of the skin or body surface of a patient 10. The patient 10 has implanted therein a typical access device 11. Such devices are sometimes referred to as implantable vascular access devices and are utilized on patients who require extensive and periodic therapy such as the infusion of blood products, chemotherapy and so on. Hence the patient's body is associated with the port 11. Into port 11 the cannula 26 is emplaced. The emplacement of the cannula 26 is accommodated by a nurse or practitioner by grasping the winged members 23 and 24 and utilizing those members to direct the end of the cannula 26 into the port 11. This aspect or operation of the device is shown for example in FIG. 5 and FIG. 6 whereby the winged members 23 and 24 are grasped by the hand or fingers of the practitioner 50. In this manner, the practitioner can direct the cannula into the port 11 associated with the patient.

As seen in FIG. 1, the cannula is directed through the body of the disc 20 such that a first portion of the cannula is embedded within the disc and lodged between sections A and B. The cannula is a thin needle having a sharpened point for insertion into the access port 11 and is bent at 90° with a first portion of the bent cannula embedded with the disc housing. The output of the cannula which is also designated as 26 is directed from the input end of the infusion device 20 via the input port end 25. It is then glued to a clear plastic tube 28 which tube may be further coupled to a Y site arrangement 29.

The arrangement 29 has one leg of the Y which is adapted to have a needle inserted into the end 33 for the administration of special chemicals to the patient. The other end of the Y as 34 is coupled via an additional tube 35 to an additional output port 32 and is associated with a typical clamping device 30. The output port 32 has a removable top which can then couple the device to a source of suitable chemicals such as an infusion pump, an IV unit or some other apparatus or reservoir in order to administer the suitable body fluids to the patient having the implantable access port 11.

In any event, as can be ascertained, the exact nature of the device 20 is depicted in the various Figures. Hence again referring to FIG. 2, there is shown a side view of the device again indicating that there is a bottom housing section B and a top housing section A. Essentially, these housings are shown in greater detail and as will be explained.

Figure 3:
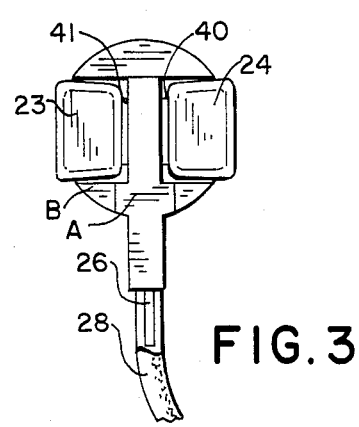
FIG. 3 is a top plan view of the infusion apparatus.

Referring to FIG. 3, as indicated, there is depicted a top view of the apparatus shown in FIG. 1. As one can ascertain, the section A fits into section B and section A is associated with the winged gripping members 23 and 24 which are coupled to the main body of the section A by means of the reduced material hinges 40 and 41.

Figure 4:
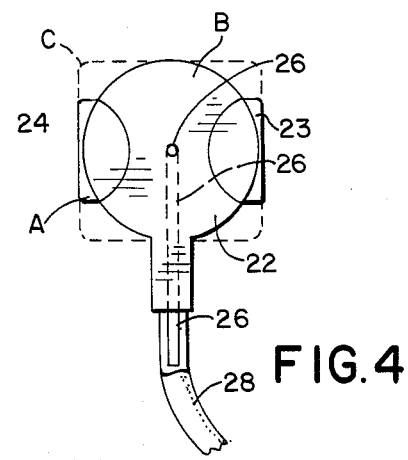
FIG. 4 is a bottom plan view of the infusion apparatus.

FIG. 4 shows a bottom view whereby it is seen that the hinge members 23 and 24 are practically encompassed within the circular profile of the disc 20 as further evidenced by the bottom section 22 of the disc. Also shown in FIG. 4 is the output portion of the cannula 26 which is coupled to the tube 28 and is secured thereto by means of a suitable glue or otherwise.

Figure 2:
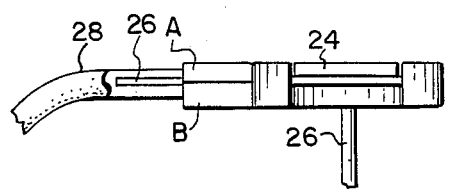
FIG. 2 is a side view of the unit of FIG. 1.
Figure 5:
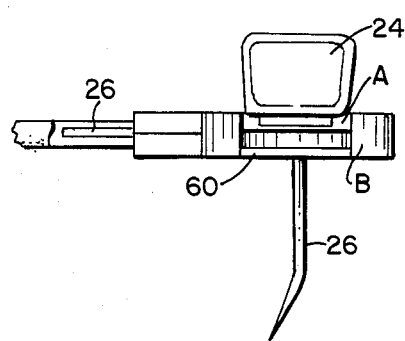
FIG. 5 is a side view showing the winged members in a upright position.
Figure 6:
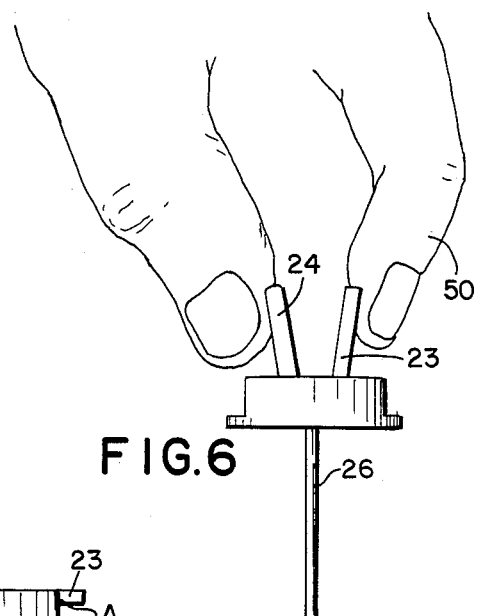
FIG. 6 is a front view depicting the wing members as being grasped by a typical operator.

FIG. 5 shows a side view which is similar to the view of FIG. 2 showing the wings as 23 and 24 in an extended position while FIG. 6 shows exactly how the wings 23 and 24 are grasped in order to enable a practitioner to manipulate the cannula 26 so that it can be inserted into the access port 11. As one can ascertain for example from looking at the side view of FIG. 2, the entire device is extremely compact and has a relatively smooth profile. Hence once the cannula is emplaced in the port 11, one can utilize a minimum amount of tape in order to secure the device to the skin of the patient. It is further understood that the wings 23 and 24 due to hysteresis of the plastic lie completely flat and in no manner can either wing touch the skin of a patient thereby enabling a practitioner to manipulate the device without the use of gloves and so on. This is an extreme improvement over prior art devices where the gripping members actually came into direct contact with the skin.

It is further understood that the entire device as shown in FIG. 2 has a completely uniform and smooth profile. The wings once grasped as shown in FIG. 6 will spring back to their position as for example shown in Figure 2 where they lie flat and are accommodated within the partial apertures as aperture 24 located on both sides of the unit and associated with section B of the unit.

Figure 7:
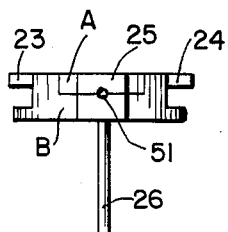
FIG. 7 is a rear view depicting the apparatus.
Figure 7A:
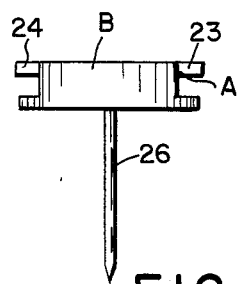

Referring to FIG. 7, there is shown a rear view which indicates the composite nature of the disc 20 having a section A and a section B. The input port end 25 of the unit is composite and forms an output aperture 51 which aperture accommodates the extending section 26 of the cannula as for example shown in FIG. 1.

Figure 8:
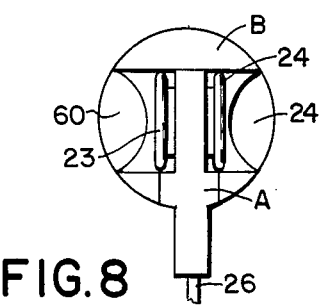
FIG. 8 is a top view showing the winged members in an upright position.

Referring to FIG. 8, there is shown a top view of the unit with the winged members 23 and 24 in the position as shown for example in FIG. 6. As one can ascertain, there are two cavities or partial apertures as 24 and 60 on the left and right sides. These apertures accommodate the wing sections and essentially each wing section can be pushed downwardly into the aperture when the tape is emplaced further assuring that they will not contact the skin of the patient.

Figure 9:
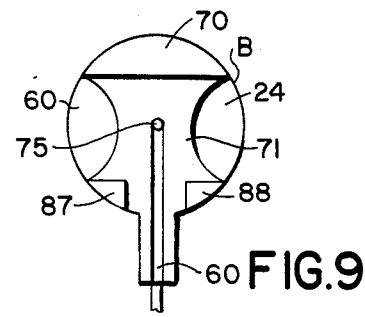
FIG. 9 is a top plan view showing one section of the composite device.
Figure 10:
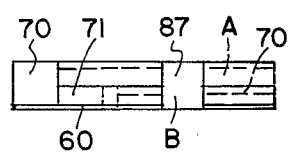
FIG. 10 is a side view showing the one section in a side elevation view as section 9.

Referring to FIG. 9, there is shown a top plan view of the bottom section B. Essentially, the bottom section B consists of a top ridge 70 of semicircular configuration being of a greater height than a central ridge 71. The central ridge 71 has a partial channel 60 directed on the surface 10 cooperating with a full aperture 75 to allow the cannula to project from the bottom surface. The portions shown in FIG. 9 as 24 and 60 are thin and are integral with the central portion 71 which as shown for example in the side view of FIG. 10 is of a greater dimension than section 60 and section 24.

Figure 11:
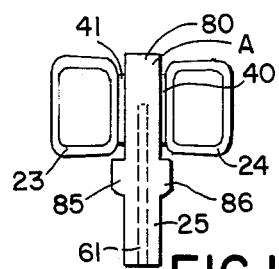
FIG. 11 is a top plan view showing the other section of the composite device.

Referring to FIG. 11, there is shown a top view of section A of the composite disc body. Essentially, section A consists of a center portion 80 which is relatively rectangular and planar and having a corresponding channel 61 which cooperates with channel 60 in section A to form a composite cannula accommodating channel. The central section 80 of section A is coupled to the two winged members via the hinge portions 41 and 40 which are integrally formed during the injection molding technique. The section A also has two semicircular projections as 85 and 86 which abut against the upstanding projections as 87 and 88 of section B to enable the accurate alignment of the partial channel 60 with the partial channel 61 when section A is emplaced within section B as shown by the dashed lines of FIG. 10.

Figure 12:
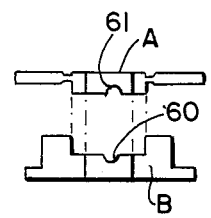
FIG. 12 is an assembly view showing the top section positioned above and about to be inserted into the bottom section.

Referring to FIG. 12, there is shown section A positioned directly above section B whereby section A has the partial aperture indicative of channel 61 and section B has the partial aperture indicative of channel 60. The needle or cannula is emplaced in the section B with the sharpened end of the needle 26 directed through the aperture 75 with a first length of the needle placed within the partial channel 60. Then section A is emplaced upon section B as shown in FIG. 12. In this position, with the needle inserted, the units are secured together by means of conventional plastic securing techniques such as an ultrasonic welding technique or the use of an epoxy or suitable glue.

Hence the needle is welded or embedded within the body of the disc for increased stability and has therefore much less chance of separation. The tubing as 28 is glued to the cannula at the input port 25 as shown in FIG. 1 and#FIG. 2 and this operates to prevent leakage and inadvertent separation. As one can ascertain, the cannula 26 is centrally located in the body of the disc and completely embedded in the body of the disc.

In this manner, this structure allows the dressing to be centered over the entire unit thus giving maximum support at the desired location. This gives added strength and with the dressing helps to eliminate infection. The wings as for example 23 and 24 would serve as user-friendly devices and allows one to grip the disc body via the wings for insertion of the needle into the port 11. Once the needle is inserted, the wings lie flat and are coextensive with the top profile of the entire unit as shown in FIG. 2. This gives the entire unit an extremely smooth profile which further prevents, due to the centering of the needle, the rocking or movement of the unit during the course of the day. This is afforded by placing the center of gravity over the top of the implantable port 11.

Hence once the unit is taped in position, the taping procedure will actually operate to push the needle further down into the port 11. Thus the entire structure provides maximum benefits, allows for easy insertion and is a simple unit to use. The entire disc basically is approximately 2.0 cm. in diameter with a height of ½ cm. The length of the disc from the edge of the input port 25 to the end is approximately 2.5 cm. The wings are generally rectangular in shape but have a slightly larger outer edge than the inner edge and hence taper inwardly on both sides. The length of the outer edge of each wing is approximately 1 cm with the length of the inner edge of the wings being approximately 0.9 cm.

It is understood that the above-noted dimensions are given by way of an example and for example, different cannula sizes or gauges can be utilized with the discs shown in the specification to accommodate different patient requirements in different infusion techniques. It is also immediately ascertained that while the tube 28 which is coupled to the output port of the cannula 26 is shown coupled to a Y site type of arrangement, it is immediately noted that this can be coupled to a single output port where the Y section can be eliminated and the tube 28 directly coupled to an output port with a clamping mechanism such as 30 utilized in conjunction therewith.

It is the main aspect of the present invention to provide a winged infusion set whereby one has grasping means in the nature of winged devices at the right and left sides of a symmetrical disc whereby the wings when grasped enable a practitioner to insert the cannula which is centrally located on the disc into a vascular access port such as port 11 associated and mounted on the skin or the body of a patient. Once the unit is inserted, the wings will spring back to their original position thus creating an extremely flat profile for the entire unit whereby the unit can be taped in position further assuring proper location while preventing the rocking or accidental dislodgement of the entire system during use by the patient.

Thus the winged devices as indicated spring back into position and hence are flush with the top surface of the disc in order to allow a tape or surgical dressing to easily hold the entire unit in place. The cannula is centered with respect to the major axis of the disc and therefore eliminates undesired movements of the device. This all operates to provide a more efficient device in conjunction with a implantable vascular access port as port 11.

As indicated there are many different types of cannulas in regard to size or gauge which can be employed to accommodate various different needs as may be required.

What is claimed is:

1. An infusion apparatus for use with an implantable access port which port is positioned on a body surface of a patient to allow the patient to receive various fluids and chemicals for treatment, comprising:
   a disc housing assembly having a top and bottom surface separated by a circumferential sidewall,
   a cannula imbedded in said disc for a given length and extending from the central region of said bottom surface and adapted to be inserted into said access port,
   first and second winged members hingedly secured to said top surface of said disc and oriented so that in a first position they are relatively flush with said surface and contained within said surface area and capable of being grasped so that in a second position they are positioned transverse to said surface to allow insertion of said cannula into said access port, wherein when said winged members are released they spring back to assume said first position, whereby said first and said second winged members are flush with said top surface of said disc housing and cannot contact said body surface of said patient due to said separation between said bottom surface and said top surface of said housing afforded by said circumferential sidewall.

2. The infusion apparatus according to claim 1, wherein said disc has an extending input port section directed from said sidewall and positioned to enable a portion of said cannula to extend from said port to allow coupling to a delivery tube.

3. The infusion apparatus according to claim 1, wherein said disc is a composition housing having a bottom circular housing section including a cannula accommodating channel coextensive with an aperture to allow said cannula to be directed from the center of the bottom surface of said circular housing section and a top housing section having a corresponding channel and having a planar central portion, with said winged members hingedly secured thereto at right and left sides with said top housing secured to said bottom housing such that said winged members are contained within said surface area of said bottom housing, with said given length of said cannula imbedded between said top and bottom housing sections as accommodated within said channels.

4. The infusion apparatus according to claim 3, wherein said cannula is ultrasonically welded to said top and bottom sections.

5. The infusion apparatus according to claim 3, wherein said winged members are integrally formed with said top section by means of reduced cross sectional area hinge areas closest to said planar central portion.

6. The infusion apparatus according to claim 1, wherein said disc housing is fabricated from plastic.

7. The infusion apparatus according to claim 1, wherein said sidewall is of a height substantially less than the diameter of said disc.

8. The infusion apparatus according to claim 1, wherein said disc assembly is circular in configuration.

9. The infusion apparatus according to claim 1, wherein said disc assembly is rectangular in configuration.

10. An infusion apparatus for use with an implantable access device having a port which port is positioned on a body surface of a patient to allow the patient to receive various fluid and chemicals for treatment administered by a practitioner, said infusion apparatus of the type having a cannula directed from a housing to enable insertion of said cannula into said port, the improvement in combination therewith of,
a relatively symmetrical housing having a bottom surface from which said cannula extends at a central portion from said surface and directed relatively transverse thereto, with another portion of said cannula firmly embedded within said housing and having an end directed from said housing for coupling to a delivery tube, said housing having
a top surface separated a given distance from said bottom surface by a circumferential sidewall and including left and right winged members hingedly secured to said top surface of said relatively symmetrical housing, said left and right winged members being flush with said top surface in a first position and capable when grasped by said practitioner of extending transverse to said top surface in a second position to enable said practitioner when grasping said left and said right winged members to manipulate and insert said cannula into said access port whereby when said left and said right members are no longer grasped, said members return to said first position and cannot contact said body surface of said patient due to said separation between said bottom surface and said top surface of said housing afforded by said circumferential detail.

11. The apparatus according to claim 10, wherein said symmetrical housing is a disc shaped housing of a circular configuration.

12. The apparatus according to claim 10, wherein said another portion of said cannula is welded within said housing.

13. The apparatus according to claim 10, wherein said housing is fabricated from plastic.

14. The infusion apparatus according to claim 11, wherein said disc housing is a composite housing having a bottom circular housing section including a cannula accommodating channel coextensive with an aperture centrally located to allow said cannula to be directed from a bottom surface of said housing and a top housing section having a corresponding channel and having a planar central portion having first a left and right hinged winged matter extending from left and right sides of said top housing section such that said winged members are contained within said surface area of said bottom housing section with a given length of said cannula embedded between said sections as accommodated within said channels.

15. The infusion apparatus according to claim 14, wherein said cannula is welded to said sections.

16. An infusion apparatus for use with an implantable access port which port is positioned on a body surface of a patient to allow the patient to receive various fluids and chemicals for treatment, comprising
a complete disc housing assembly having a top surface and a bottom surface separated by a circumferential sidewall said housing assembly having a bottom circular housing section including a cannula accommodating channel coextensive with an aperture located in the center of the bottom surface of said bottom circular housing section and a top housing section having a corresponding channel and having a planar central portion;
a cannula located between said bottom circular housing section and extending for a given length from the central region of said bottom surface and adapted to be inserted into said access port, said given length of said cannula being embedded between said top and said bottom housing sections with said top housing section secured to said bottom housing section;
first and second winged members hingedly secured at right and left sides to said planar central portion of said top housing section and oriented so that in a first position they are relatively flush with said top housing section and contained within said surface area of said bottom housing section and capable of being grasped so that in a second position they are positioned transverse to said top housing section to allow insertion of said cannula into said access port wherein when said winged members are released they spring back to assume said first position whereby said first and said second winged members are flush with said top housing section and cannot contact said body surface of said patient due to said separation between said bottom surface and said top surface of said housing afforded by said circumferential sidewall.

* * * * *